United States Patent

Beard et al.

[11] 4,011,320
[45] Mar. 8, 1977

[54] 7(8)-SUBSTITUTED TRIAZINOBENZIMIDAZOLES AND ANTHELMINTIC COMPOSITIONS AND METHOD

[75] Inventors: Colin C. Beard, Palo Alto; John A. Edwards, Los Altos; John H. Fried, Palo Alto, all of Calif.

[73] Assignee: Syntex (U.S.A.) Inc., Palo Alto, Calif.

[22] Filed: Mar. 8, 1976

[21] Appl. No.: 664,454

Related U.S. Application Data

[63] Continuation-in-part of Ser. No. 589,237, June 23, 1975, abandoned.

[52] U.S. Cl. .............................. 424/249; 260/249.5
[51] Int. Cl.$^2$ ...................................... C07D 251/72
[58] Field of Search ................. 260/249.5; 424/249

[56] References Cited

UNITED STATES PATENTS 3,896,120  7/1975  Rochling et al. ............... 260/249.5

*Primary Examiner*—John M. Ford
*Attorney, Agent, or Firm*—Joseph I. Hirsch; William B. Walker

[57] ABSTRACT

7(8)-substituted triazinobenzimidazoles represented by the formula:

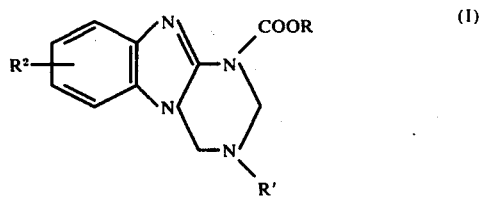

where R is a lower alkyl group having 1 to 4 carbon atoms; R' is diloweralkylaminoalkyl ($C_{2-6}$) or alkyl having 1 to 18 carbon atoms; $R^2$ is phenylsulfinyl, phenoxyethoxy, benzyloxyethoxy, methoxyethylsulfinyl, or 3-chloroprop-1-ylsulfinyl; the $R^2$-substitution being at the 7(8)-position; or a pharmaceutically acceptable salt thereof.

The compounds are useful as pesticides, particularly as antifungal and anthelmintic agents.

31 Claims, No Drawings

7(8)-SUBSTITUTED TRIAZINOBENZIMIDAZOLES AND ANTHELMINTIC COMPOSITIONS AND METHOD

REFERENCE TO PARENT APPLICATION

This application is a continuation-in-part of application Ser. No. 589,237, filed June 23, 1957, now abandoned.

FIELD OF THE INVENTION

This invention relates to novel, chemical compounds. More particularly, this invention relates to novel antifungal and anthelmintic triazinobenzimidazoles which are substituted at the 7(8)-position.

BACKGROUND OF THE INVENTION

Antifungically active and anthelmintically active triazinobenzimidazoles unsubstituted at the 7(8)-position are described in U.S. Pat. No. 3,896,120. Benzimidazole-2-carbamates substituted with the $R^2$-substituents set forth herein are described in pending application Ser. Nos. 417,963, filed Nov. 21, 1973, now U.S. Pat. No. 3,929,821, and 526,861, filed Nov. 25, 1974, now U.S. Pat. No. 3,929,824.

SUMMARY OF THE INVENTION

The novel 7(8)-substituted triazinobenzimidazoles of the present invention are presented by the following formula:

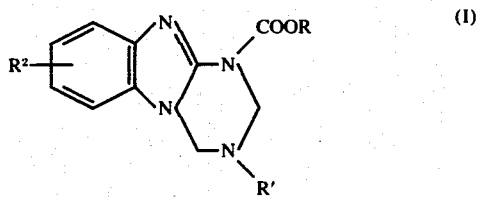

where R is a lower alkyl group having 1 to 4 carbon atoms, $R^1$ is alkyl having 1 to 18 carbon atoms or diloweralkylaminoalkyl ($C_{2-6}$); $R^2$ is phenylsulfinyl, phenoxyethoxy, benzyloxyethoxy, methoxyethylsulfinyl, or 3-chloroprop-1-ylsulfinyl; the $R^2$-substituent being at the 7(8)-position, or a pharmaceutically acceptable salt thereof.

As used in this specification and claims, the term "lower alkyl" refers to both straight and branched chain alkyl groups having a total of 1 through 4 carbon atoms and, thus, includes methyl, ethyl, n-propyl, i-propyl, n-butyl, ibutyl, and t-butyl. The term "alkyl" refers to straight and branched chain alkyl groups having from 2 through 6 carbon atoms (for example, ethyl, n-propyl, i-propyl, n-butyl, n-pentyl, n-hexyl, and the like) of from 1 through 18 carbon atoms (for example, methyl, ethyl, n-propyl, i-propyl, n-butyl, n-pentyl, n-hexyl, n-nonyl, n-decyl, n-dodecyl, n-hexadecyl, n-octadecyl, and the like) as the case may be.

The compounds of the present invention, and the pharmaceutically acceptable salts thereof, possess broad spectrum activity against parasites of mammals (human or animal), including both mature and immature parasitic forms, as represented for example, by the genera Trichostronglylus, Haemonchus, Ostertagia, Cooperia, Nematodirus, and Stronglyoides, and specifically, for example against *Nematospiroides dubius*, *Hymenolepis Nana*, *Syphacia obvelata*, and/or *Aspiculuris tetraptera*. In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

Where the compound has a basic moiety, the term pharmaceutically acceptable salts of the compounds of this invention includes those salts prepared from non-toxic inorganic or organic acids, such as those salts conventionally used in the art. Such non-toxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like. Where the compound has an acidic moiety, the term pharmaceutically acceptable salts includes those salts prepared from non-toxic bases such as, for example, the salts of sodium, potassium, lithium, copper, ammonium, and the like.

The amount of the compound to be administered will depend upon the actual compound utilized, and upon the weight of the animal being treated. In general, however, the daily dosage level will usually be between about 0.5 mg/kg and 100 mg/kg of body weight of the animal being treated. The active ingredient is adapted to be administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

The compounds of the present invention can be prepared from the corresponding 5(6)-substituted-benzimidazole-2-carbamate, alkyl ($C_{1-18}$) amine or N,N-(diloweralkyl)alkylenediamine ($C_{2-6}$) in the presence of at least two moles of formaldehyde in aqueous solution. The reaction is conducted in an inert organic solvent, such as benzene, diethyl ether, acetone, chloroform, methylene chloride, preferably methylene chloride, or the like, at a temperature from about 0° C to about 80° C, preferably about 20° C to about 40° C for about 1 hour to about 24 hours. The desired product is separated from the reaction mixture and purified by suitable procedures. For example, typical separation procedures include filtration, extraction, evaporation, and typical purification procedures include crystallization, and both thin-layer and column chromatography. Optimum separation and purification procedures can be determined by routine experimentation as would apparent to those skilled in this art.

Exemplary of the compounds of the present invention, as represented by Formula I above, are the following illustrative compounds:

1-methoxycarbonyl-3-methyl-7(8)-phenylsulfinyl-1,2,3,4-tetrahydro-S-triazino[1,2-a]benzimidazole;
1-methoxycarbonyl-3-n-butyl-7(8)-phenylsulfinyl-1,2,3,4-tetrahydro-S-triazino[1,2-a]benzimidazole;
1-methoxycarbonyl-3-n-nonyl-7(8)-phenylsulfinyl-1,2,3,4-tetrahydro-S-triazino[1,2-a]benzimidazole;
1-methoxycarbonyl-3-n-octadecyl-7(8)-phenylsulfinyl-1,2,3,4-tetrahydro-S-triazino[1,2-a]benzimidazole;
1-methoxycarbonyl-3-[2-(N,N-dimethylamino)ethyl]-7(8)-phenylsulfinyl-1,2,3,4-tetrahydro-S-triazino[1,2-a]benzimidazole;
1-methoxycarbonyl-3-[2-(N,N-diethylamino)ethyl]-7(8)-phenylsulfinyl-1,2,3,4-tetrahydro-S-traizino[1,2-a]benzimidazole;
1-methoxycarbonyl-3-[2-(N,N-di(n-butyl)amino)ethyl]-7(8)-phenylsulfinyl-1,2,3,4-tetrahydro-S-triazino[1,2-a]benzimidazole;
1-methoxycarbonyl-3-[4-(N,N-dimethylamino)butyl]-7(8)-phenylsulfinyl-1,2,3,4-tetrahydro-S-triazino[1,2-a]benzimidazole;
1-methoxycarbonyl-3-[6-(N,N-dimethylamino)hexyl]-7(8)-phenylsulfinyl-1,2,3,4-tetrahydro-S-triazino[1,2-a]benzimidazole;
1-methoxycarbonyl-3-methyl-7(8)-phenoxyethoxy-1,2,3,4-tetrahydro-S-triazino[1,2-a]benzimidazole;
1-methoxycarbonyl-3-n-butyl-7(8)-phenoxyethoxy-1,2,3,4-tetrahydro-S-triazino[1,2-a]benzimidazole;
1-methoxycarbonyl-3-n-nonyl-7(8)-phenoxyethoxy-1,2,3,4-tetrahydro-S-triazino[1,2-]benzimidazole;
1-methoxycarbonyl-3-n-octadecyl-7(8)-phenoxyethoxy-1,2,3,4-tetrahydro-S-triazino[1,2-a]benzimidazole;
1-methoxycarbonyl-3-[2-(N,N-dimethylamino)ethyl]-7(8)-phenoxyethoxy-1,2,3,4-tetrahydro-S-triazino[1,2-a]benzimidazole;
1-methoxycarbonyl-3-[2-(N,N-diethylamino)ethyl]-7(8)-phenoxyethoxy-1,2,3,4-tetrahydro-S-triazino[1,2-a]benzimidazole;
1-methoxycarbonyl-3-[2-(N,N-di(n-butyl)amino)ethyl]-7(8)-phenoxyethoxy-1,2,3,4-tetrahydro-S-triazino[1,2-a]benzimidazole;
1-methoxycarbonyl-3-[4-(N,N-dimethylamino)butyl]-7(8)-phenoxyethoxy-1,2,3,4-tetrahydro-S-triazino[1,2-a]benzimidazole;
1-methoxycarbonyl-3-[6-(N,N-dimethylamino)hexyl]-7(8)-phenoxyethoxy-1,2,3,4-tetrahydro-S-triazino[1,2-a]benzimidazole;
1-methoxycarbonyl-3-methyl-7(8)-bensyloxyethoxy-1,2,3,4-tetrahydro-S-triazino[1,2-a])-benzyloxyethoxy-
1-methoxycarbonyl-3-n-butyl-7(8)-benzyloxyethoxy-1,2,3,4-tetrahydro-S-triazino[1,2-a]benzimidazole;
1-methoxycarbonyl-3-n-nonyl-7(8)-benzyloxyethoxy-1,2,3,4-tetrahydro-S-triazino[1,2-a]benzimidazole;
1-methoxycarbonyl-3-n-octadecyl-7(8)-benzyloxyethoxy-1,2,3,4-tetrahydro-S-triazino[1,2-a]benzimidazole;
1-methoxycarbonyl-3-[2-(N,N-dimethylamino)ethyl]-7(8)-benzyloxyethoxy-1,2,3,4-tetrahydro-S-triazino[1,2-a]benzimidazole;
1-methoxycarbonyl-3-[2-(N,N-diethylamino)ethyl]7(8)-benzyloxyethoxy-1,2,3,4-tetrahydro-S-triazino[1,2-a]benzimidazole;
1-methoxycarbonyl-3-[2-(N,N-di(n-butyl)amino)ethyl]7(8)-benzyloxyethoxy-1,2,3,4-tetrahydro-S-triazino[1,2-a]benzimidazole;
1-methoxycarbonyl-3-[4-(N,N-dimethylamino)butyl]-7(8)-benzyloxyethoxy-1,2,3,4-tetrahydro-S-triazino[1,2-a]benzimidazole;
1-methoxycarbonyl-3-[6-(N,N-dimethylamino)hexyl]-7(8)-benzyloxyethoxy-1,2,3,4-tetrahydro-S-triazino[1,2-a]benzimidazole;
1-methoxycarbonyl-3-methyl-7(8)-methoxyethylsulfinyl-1,2,3,4-tetrahydro-S-triazino[1,2-a]benzimidazole;
1-methoxycarbonyl-3-n-butyl-7(8)-methoxyethylsulfinyl-1,2,3,4-tetrahydro-S-triazino[1,2-a]benzimidazole;
1-methoxycarbonyl-3-n-nonyl-7(8)-methoxyethylsulfinyl-1,2,3,4-tetrahydro-S-triazino[1,2-a]benzimidazole;
1-methoxycarbonyl-3-n-octadecyl-7(8)-methoxyethylsulfinyl-1,2,3,4-tetrahydro-S-triazino[1,2-a]benzimidazole;
1-methoxycarbonyl-3-[2-(N,N-dimethylamino)ethyl]-7(8)-methoxyethylsulfinyl-1,2,3,4-tetrahydro-S-triazino[1,2-a]benzimidazole;
1-methoxycarbonyl-3-[2-(N,N-diethylamino)ethyl]-7(8)-methoxyethylsulfinyl-1,2,3,4-tetrahydro-S-triazino[1,2-a]benzimidazole;
1-methoxycarbonyl-3-[2-(N,N-di(n-butyl)amino)ethyl]-7(8)-methoxyethylsulfinyl-1,2,3,4-tetrahydro-S-triazino[1,2-a]benzimidazole;
1-methoxycarbonyl-3-[4-(N,N-dimethylamino)butyl]-7(8)-methoxyethylsulfinyl-1,2,3,4-tetrahydro-S-triazino[1,2-a]benzimidazole;
1-methoxycarbonyl-3-[6-(N,N-dimethylamino)hexyl]-7(8)-methoxyethylsulfinyl-1,2,3,4-tetrahydro-S-triazino[1,2-a]benzimidazole;
1-methoxycarbonyl-3-methyl-7(8)-(3-chloroprop-1-ylsulfinyl)-1,2,3,4-tetrahydro-S-triazino[1,2-a]benzimidazole;
1-methoxycarbonyl-3-n-butyl-7(8)-(3-chloroprop-1-ylsulfinyl)-1,2,3,4-tetrahydro-S-triazino[1,2-a]benzimidazole;
1-methoxycarbonyl-3-n-nonyl-7(8)-(3-chloroprop-1-ylsulfinyl)-1,2,3,4-tetrahydro-S-triazino[1,2-a]benzimidazole;
1-methoxycarbonyl-3-n-octadecyl-(3-chloroprop-1-ylsulfinyl)-1,2,3,4-tetrahydro-S-triazino[1,2-a]benzimidazole;
1-methoxycarbonyl-3-[2-(N,N-dimethylamino)ethyl]-7(8)-(3-chloroprop-1-ylsulfinyl)-1,2,3,4-tetrahydro-S-triazino-[1,2-a]benzimidazole;
1-methoxycarbonyl-3-[2-(N,N-diethylamino)ethyl]-7(8)-(3-chloroprop-1-ylsulfinyl)-1,2,3,4-tetrahydro-S-triazino-[1,2-a]benzimidazole;
1-methoxycarbonyl-3-[2-(N,N-di(n-butyl)amino)ethyl]-7(8)-(3-chloroprop-1-ylsulfinyl)-1,2,3,4-tetrahydro-S-triazino-[1,2-a]benzimidazole;
1-methoxycarbonyl-3-[4-(N,N-dimethylamino)butyl]-7(8)-(3-chloroprop-1-ylsulfinyl)-1,2,3,4-tetrahydro-S-triazino-[1,2-a]benzimidazole;
1-methoxycarbonyl-3-6-(N,N-dimethylamino)hexyl]-7(8)-(3-chloroprop-1-ylsulfinyl)-1,2,3,4-tetrahydro-S-triazino-[1,2-a]benzimidazole;
and the corresponding 1-ethoxycarbonyl, 1-propoxycarbonyl or 1-butoxycarbonyl compounds.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

Unless otherwise indicated, all temperatures are in degrees centigrade and all percentages are by weight.

PREPARATION 1

6 G. of 2-nitro-4-thiocyanatoaniline in 30 ml. of dimethylformamide is treated under nitrogen with 1.2 g. of sodium borohydride at 20° to 30°. After 1½ hours 15 ml. of acetone is added, followed 2 hours later by 10 g. of 3-chloropropylbromide. The mixture is left at 20°–25° for 16 hours, then diluted with water. The oily product is extracted into chloroform and passed through a silica column. 2-Nitro-4-(3-chloropropylthio)aniline is isolated by evaporation of the solvent.

6 G of 2nitro-4-(3-chloropropylthio)aniline is treated in 120 ml. methanol and 120 ml. of water with 30 g. of sodium hydrosulfite ($Na_2S_2O_4$) on the steam bath for about 5 minutes. The reaction mixture is concentrated under vacuum and extracted well with chloroform. Evaporation of the dried extract affords 1,2-diamino-4-(3-chloropropylthio)benzene.

4G. of 1,2-diamino-4-(3-chloropropylthio)benzene and 4.2 g. of 1,3-bis(methoxycarbonyl)-S-methyl isothiourea are heated in a mixture of 40 ml. of ethanol, 40 ml. of water and 1.5 ml. of acetic acid for 4 hours at reflux. The mixture is cooled and 5(6)-(3-chloropropylthio)-2-carbomethoxyaminobenzimidazole filtered off. Recrystallization may be effected from methanol chloroform.

1.5 G. of 5(6)-(3-chloropropylthio)-2-carbomethoxyaminobenzimidazole is dissolved in 100 ml. of chloroform and 10 ml. of acetic acid at −20° . A solution of 1.05 g. of m-chloroperbenzoic acid in 30 ml. of chloroform is added and the mixture allowed to warm slowly to 20°–25°. After 3 hours at 20°–25° the mixture is concentrated under vacuum and the residue treated with sodium bicarbonate solution. The crude product is filtered off and recrystallized from methanol to afford 5(6)-(3-chloropropylsulfinyl)-2-carbomethoxyaminobenzimidazole.

PREPARATION 2

A solution of 7.5 g. of 2-benzyloxyethanol in 30 ml. of dimethylformamide is treated with 1.2 g. of sodium hydride. When the mixture is homogeneous, 3.5 g. of 2-amino-4-chloro-1-nitrobenzene is added and the mixture heated at 110°–120° for 4 hours. The mixture is cooled, diluted with water and extracted with benzene. The crude product is treated with charcoal and isolated by precipitation with cyclohexane to afford 2-amino-1-nitro-4-(2-benzyloxyethoxy)benzene.

1.6 G. of 2-amino-4-(2-benzyloxyethoxy)-1-nitrobenzene is treated in 100 ml. of methanol and 50 ml. of water with 10 g. of sodium hydrosulfite ($Na_2S_2O_4$) on the steam bath for 15 minutes. The reaction mixture is concentrated under vacuum and extracted with chloroform. Evaporation of the extract affords 1,2-diamino-4-(2-benzyloxyethoxy)benzene.

1.4 G. of 1,2-diamino-4-(2-benzyloxyethoxy)benzene and 1.4 g. of 1,3-bis(methoxycarbonyl)-S-methyl isothiourea is treated in 20 ml. of ethanol and 20 ml. of water with 0.5 ml. of acetic acid. After refluxing for 5 hours the mixture is cooled and filtered. Recrystallization of the product from methanol-chloroform affords 5(6)-(2-benzyloxyethoxy)-2-carbomethoxyaminobenzimidazole.

PREPARATION 3

5 G. of 2-amino-4-chloro-1-nitrobenzene is added to a solution of sodium phenyl mercaptide, prepared under nitrogen from 2.53 g. 57% sodium hydride and 6.2 ml. thiophenol in 20 ml. dimethylformamide, with a 10 ml. dimethylformamide rinse. The mixture is stirred under nitrogen for 3 hours at 20°–30° C and then diluted with water. The crude product is washed with water and hexane, then recrystallized from methanol, yielding 2-amino-4-phenylthio-1-nitrobenzene.

6.0 G. of 2-amino-4-phenylthio-1-nitrobenzene is dissolved in 80 ml. acetic anhydride and treated with a few drops of sulfuric acid. The mixture is left at 20°–30° C for 2 hours then a little sodium acetate added and the solvent removed under vacuum. The residue is treated with water, filtered and recrystallized from methanol yielding 2-acetamido-4-phenylthio-1-nitrobenzene. This material may also be obtained by reaction of 2-acetamido-4-chloro-1-nitrobenzene with sodium phenylmercaptide essentially as described above for the free amine.

7.0 G. of 2-acetamido-4-phenylthio-1-nitrobenzene is dissolved in 70 ml. of chloroform and treated, at −20° to −15° C, with a solution of 5.0 g. 40% peracetic acid in 10 ml. methanol. The mixture is allowed to warm slowly to 20° C and stirred for four hours. The reaction mixture is extracted with sodium bisulfite solution, then sodium bicarbonate solution, dried and evaporated. The residual gum of 2-acetamido-4-phenylsulfinyl-1-nitrobenzene is treated with 20 ml. 5N sodium hydroxide and 40 ml. methanol at 20°–25° C for one hour. Water is then added and essentially pure 2-amino-4-phenylsulfinyl-1-nitrobenzene filtered off. Recrystallization may be effected from benzene.

5.4 G. of 2-amino-4-phenylsulfinyl-1-nitrobenzen is hydrogenated at 1 atmosphere pressure in 500 ml. methanol in the presence of 5 g. 5% palladized carbon, until the theoretical uptake of hydrogen has occurred. The catalyst is removed by filtration and the filtrate stripped under vacuum. The residue is recrystallized from methanol-benzene, yielding 1,2-diamino-4-phenylsulfinylbenzene.

A mixture of 5.5 g. of 1,2-diamino-4-phenylsulfinylbenzene, 4.3 g. of 1,3-bis-methoxycarbonyl-S-methyl isothiourea and 1.2 ml. acetic acid in 100 ml. ethanol and 100 ml. water is refluxed for four hours. The mixture is cooled and essentially pure 5(6)-phenylsulfinyl-2-carbomethoxyaminobenzimidazole filtered off and washed with methanol. Recrystallization may be effected from methanolchloroform.

In a similar manner, substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea, for the 1,3-bis-methoxycarbonyl-S-methyl isothiourea, the corresponding 2-carbalkoxyamino-5(6)-phenylsulfinylbenzimidazole compounds are prepared. The 2-carbalkoxyamino analogs of the compounds of Preparations 1, 2, 4 and 5 are also prepared in a similar manner.

Preparation 4

A mixture of 2.5 g. of 4-hydroxy-6-nitroacetanilide, 2.7 g. of 2-bromoethylphenyl ether, and 3.6 g. of potassium carbonate in 25 ml. of dimethylformamide is heated to 110° C under nitrogen for 16 hours. The mixture is cooled, diluted with water, and 4-(2-phenoxyethoxy)-2-nitroacetanilide is isolated by filtration.

2.3 G. of 4-(2-phenoxyethoxy)-2-nitroacetanilide is heated for ½ hour with 5 ml. of 5N sodium hydroxide solution and 30 ml. of methanol. The mixture is cooled, diluted with water, and 4-(2-phenoxyethoxy)-2-nitroaniline isolated by filtration.

A mixture of 1.8 g. of 4-(2-phenoxyethoxy)-2-nitroaniline and 0.3 g. of 5% of palladium-on-charcoal catalyst in 200 ml. of methanol is hydrogenated under ambient conditions. After the uptake of hydrogen is complete, the mixture is filtered and 1,2-diamino-4-(2phenoxyethoxy)benzene is isolated from the filtrate by evaporation.

1.6 G. of 1,2-diamino-4-(2-phenoxyethoxy)benzene in 12 ml. of ethanol, 12 ml. of water and 0.3 ml. of acetic acid is treated with 2 g. of 1,3-bis(methoxycarbonyl)-S-methyl isothiourea, at reflux, for 4 hours. The mixture is cooled, filtered, and the product recrystallized from methanol-chlorofrom yielding 5(6)-(2-phenoxyethoxy)-2-carbomethoxyaminobenzimidazole.

Preparation 5

2.37 G. of 1-acetamido-2-nitro-4-thiocyanatobenzene in 10 ml. dimethylformamide is treated at 20°–25° C under nitrogen, with 0.38 g. of sodium borohydride. After one hour 1.6 ml. of chloroethyl methyl ether is added, and the mixture kept at 20°–30° C for a further three hours. Water is then added and the product filtered off. Recrystallization from cyclohexane gives 1-acetamido-2-nitro-4-methoxyethylthiobenzene.

1.4 G. of 1-acetamido-2-nitro-4-methoxyethylthiobenzene is treated with 3 ml. 5N sodium hydroxide and 6 ml. methanol in the steam bath for about 15 minutes. The mixture is stripped under vacuum and the residue extracted with chloroform. The dried extracts are evaporated giving 1-amino-2-nitro-4-methoxyethylthiobenzene as a red crystalline solid.

1.3 G. of 1-amino-2-nitro-4-methoxyethylthiobenzene is treated in 80 ml. methanol and 20 ml. water at reflux under nitrogen, with 0.7 g. ferrous sulfate and 2.8 g. iron (added in two portions) for 4 hours. The mixture is filtered, stripped under vacuum, and the residue recrystallized from cyclohexane. 1,2-Diamino-4-methoxymethylthiobenzene is thus obtained.

0.85 G. of 1,2-diamino-4-methoxyethylthiobenzene and 1.0 g. 1,3-bis-methoxycarbonyl-S-methyl isothiourea in 25 ml. ethanol and 25 ml. water is treated at reflux with 0.7 ml. acetic acid. After four hours the mixture is cooled and filtered, yielding 5(6)-methoxyethylthio-2-carbomethoxyaminobenzimidazole, which may be recrystallized from methanol-chloroform.

1.8 G. of 5(6)-methoxyethylthio-2-carbomethoxyaminobenzimidazole in 200 ml. of chloroform and 1 ml. of acetic acid is treated with 1.55 g. of 30% peracetic acid in acetic acid solution at 15° C. The solution is stirred for 1 hour and then evaporated. The residue is triturated with diethylether and the solid is collected by filtration. Recrystallization from methanol-chloroform gives 5(6)-(2-methoxyethylsulfinyl)-2-carbomethoxyaminobenzimidazole.

EXAMPLE 1

A mixture of 1.2 g. of 5(6)-phenylsulfinyl-2-carbomethoxyaminobenzimidazole, 1 ml. of butylamine and 3 ml. of 37% formaldehyde in 120 ml. of methylene chloride is refluxed gently for about 12 hours. The mixture is cooled, washed with water, dried over magnesium sulfate and the solvent removed under vacuum at about 20° C. The residue is recrystallized from ether to afford 1-methoxycarbonyl-3-n-butyl-7(8)-phenylsulfinyl-1,2,3,4-tetrahydro-S-triazino[1,2-a]benzimidazole. [m.p. 116°–136° C (dec); uv 223, 296 nm ($\epsilon$ 45600, 17400)].

In similar manner, substituting 5(6)-phenoxyethoxy-2-carbomethoxyaminobenzimidazole, 5(6)-benzyloxyethoxy-2-carbomethoxyaminobenzimidazole, 5(6)-methoxyethylsulfinyl-2-carbomethoxyaminobenzimidazole, or 5(6)-(3-chloroprop-1-ylsulfinyl)-2-carbomethoxyaminobenzimidazole, for the 5(6)-phenylsulfinyl-2-carbomethoxyaminobenzimidazole, the corresponding 1-methoxycarbonyl-3-n-butyl-7(8)-substituted-1,2,3,4-tetrahydro-S-triazino[1,2-a]benzimidazoles are prepared.

EXAMPLE 2

The procedure of Example 1 is repeated substituting 1.2 ml. N,N-dimethylethylenediamine for the n-butylamine. After refluxing for 12 hours, the methylene chloride solution is washed with water, dried and passed through a short column of neutral alumina. Evaporation of the eluate under vacuum affords 1-methoxycarbonyl-3-[2-(N,N-dimethylamino)ethyl]-7(8)-phenylsulfinyl-1,2,3,4-tetrahydro-S-triazino[1,2-a]benzimidazole as an amorphous solid [uv: 230, 297 nm ($\epsilon$ 36000, 13900)].

In similar manner, substituting 5(6)-phenoxyethoxy-2-carbomethoxyaminobenzimidazole, 5(6)-benzyloxyethoxy-2-carbomethoxyaminobenzimidaozle, 5(6)-methoxyethylsulfinyl-2-carbomethoxyaminobenzimidazole, or 5(6)-(3-chloroprop-1-ylsulfinyl)-2-carbomethoxyaminobenzimidazole, for the 5(6)-phenylsulfinyl-2-carbomethoxyaminobenzimidazole, the corresponding 1-methoxycarbonyl-3-[2-(N,N-dimethylamino)ethyl]-7(8)-substituted-1,2,3,4-tetrahydro-S-triazino[1,2-a]benzimidazoles are prepared.

EXAMPLE 3

A mixture of 1.2 g. of 5(6)-phenylsulfinyl-2-carbomethoxyaminobenzimidazole and 0.55 g. of n-nonylamine in 100 ml. of methylene chloride is treated with 2 ml. of 37% formaldehyde solution. The mixture is heated to reflux for 3 hours. The resulting solution is cooled and washed with water. The methylene chloride layer is dried over sodium sulfate and is evaporated to dryness. The resulting oil is treated with ether and the mixture is filtered. The ether is displaced with hexane and the mixture cooled and filtered to afford 1-methoxycarbonyl-3-n-nonyl-7(8)-phenylsulfinyl-1,2,3,4-tetrahydro-S-triazino-[1,2-a]benzimidazole [m.p. 91°–93° C].

In similar manner, substituting 5(6)-benzyloxyethoxy-2-carbomethoxyaminobenzimidazole, 5(6)-methoxyethylsulfinyl-2-carbomethoxyaminobenzimidazole, or 5(6)-(3-chloroprop-1-ylsulfinyl)-2-carbomethoxyaminobenzimidazole, for the 5(6)-phenylsulfinyl-2-carbomethoxyaminobenzimidazole, the corresponding 1-methoxycarbonyl-3-n-nonyl-7(8)-substituted-1,2,3,4-tetrahydro-S-triazino[1,2-a]benzimidazoles are prepared.

EXAMPLE 4

The procedure of Example 3 is repeated using 1.2 g. of 5(6)-phenoxyethoxy-2-carbomethoxyaminobenzimidazole and 0.5 g. of n-nonylamine to afford 1-methoxycarbonyl-3-n-nonyl-7(8)-phenoxyethoxy-1,2,3,4-tetrahydro-S-triazino[1,2-a]-benzimidazoles [m.p. 89°–92° C].

EXAMPLES 5–8

The procedure of Example 1 is repeated substituting methylamine, n-dodecylamine, N,N-di-(n-butyl)ethylene diamine, and N,N-dimethylhexylene diamine for the n-butylamine to afford 1-methoxycarbonyl-3-methyl-7(8)-phenylsulfinyl-1,2,3,4-tetrahydro-S-triazino[1,2-a]benzimidazole, 1methoxycarbonyl-3-n-dodecylamine-7(8)-phenylsulfinyl-1,2,3,4-tetrahydro-S-triazino[1,2-a]benzimidazole, 1-methoxycarbonyl-3-[2-(N,N-di-(n-butylamino)ethyl]-7(8)-phenylsulfinyl-1,2,3,4-tetrahydro-S-triazino[1,2-a]benzimidazole, and 1-methoxycarbonyl-3-[6-(N,N-dimethylamino)ethyl]-7(8)-phenylsulfinyl-1,2,3,4-tetrahydro-S-triazino[1,2-a]benzimidazole, respectively.

In similar manner to any of the procedures set forth above, substituting the 5(6)-substituted-2-carbethoxyamino (or carbopropoxyamino or carbobutoxyamino)benzimidazoles for the carbomethoxyaminobenzimidazoles, the corresponding 1-ethoxycarboxy(or propoxycarbonyl or butoxycarbonyl)-triazino[1,2-a]benzimidazoles are prepared.

The compounds of this invention, as prepared for example in the Examples above, are considered to be a mixture of isomers where the $R^2$-substituent is at the 7- or 8-position. Such isomeric mixtures can be separated, by means conventional in this art, into the individual isomers if desired, and it is considered that such isomers will have anthelmintic and antifungal activity as do the isomeric mixtures from which they are separated.

EXAMPLE 9

Four young Swiss-Webster male mice (16–20 g.) are artificially infected with 200 larvae of the species *Nematospiroides dubius* (roundworm) and *Hymenolepis nana* (tapeworm) and naturally injected with 15–40 larvae of *Syphacia obvelata* and *Aspiculuris tetraptera* (pinworms). The drug is administered in a commerical rat/mouse diet at the stated doses from day 1 through day 18, the infection being introduced at day 0. The animals are sacrificed at day 18 and the parasites remaining in the entire small intestine, cecum and large bowel are counted and differentiated. The average number of each parasite remaining in each medicated group is compared to the average number remaining in the control. This comparison is expressed as percent reduction over the parasites in the control group. The data for illustrative compounds of this invention is tabulated in the Table below.

EXAMPLE 10

A formulation is prepared having the following composition:

| | |
|---|---|
| 1-methoxycarbonyl-3-n-butyl-7(8)-phenylsulfinyl-triazino-[1,2-a]benzimidazole | 30% |
| polyethylene glycol 6000 | 40% |
| Myrj 52 [polyoxy(40) stearate; a product of Atlas Chemical Co.] | 30% |

This formulation is prepared by heating the polyethylene glycol 6000 and Myrj 52 to 55°–60° C, and, when completely melted, the 1-methoxycarbonyl-3-n-butyl-7(8)-phenylsulfinyltriazino[1,2-a]benzimidazole is added with stirring until homogeneous. The formulation is solidified by cooling and ground, without remelting of the polyethylene glycol, to a fine powder.

EXAMPLE 11

A drench powder is prepared having the following composition:

| | |
|---|---|
| The formulation of Example 10 | 15.1 g. |
| Cabosil M-5 (colloidal silica; Cabot corp.) | 6.0 g. |
| Carboxymethyl cellulose (7M8-SXF) | 6.0 g. |

The colmelt formulation and carboxymethyl cellulose are blended together until uniform, then the Cabosil is added, the mixture blended until once again uniform, and then finely powdered.

EXAMPLE 12

A suspension is prepared having the following formulation:

| | |
|---|---|
| The formulation of Example 10 | 7.550 g. |
| Citric acid, hydrous | 0.431 g. |
| sodium citrate | 0.868 g. |
| carboxymethyl cellulose (7M8-SXF) | 1.051 g. |
| Cabosil M-5 | 1.000 g. |
| sorbic acid | .300 g. |
| purified water | to 100.00 ml. |

The sorbic acid, citric acid and sodium citrate are added to 90 ml. of water which has been heated to 80° C. The Cabosil and carboxymethyl cellulose are then added, with stirring, until uniformly dispersed and fully hydrated. The mixture is cooled to 45° C, and the formulation of Example 10 is added, with stirring, until it is uniformly dispersed. The suspension is cooled to room temperature and the balance of the water is added.

TABLE I

| R | $R^1$ | $R^2$ | dose, ppm | Nd | Hn | So | At |
|---|---|---|---|---|---|---|---|
| $CH_3$ | n-butyl | phenylsulfinyl | 125 | 100 | 100 | 100 | 100 |
| | | | 62 | 77 | 37 | 100 | 100 |
| $CH_3$ | $(CH_3)_2NCH_2CH_2-$ | phenylsulfinyl | 125 | 86 | 77 | 100 | 100 |
| | | | 62 | 59 | 0 | 100 | 100 |

Nd = Nematospiroides dubius
Hn = Hymenolepis nana
So = Syphacia obvelata
At = Aspiculuris tetraptera

EXAMPLE 13

A top dressing for horses is prepared having the following composition:

| | |
|---|---|
| The formulation of Example 10 | 8.550 g. |
| granular sucrose | 17.450 g. |
| | 25.000 g. |
| water | 1.00 ml. |

EXAMPLE 14

A top dressing for cattle is prepared having the following composition:

| | |
|---|---|
| The formulation of Example 10 | 75.52 g. |
| Soybean meal | 2196.30 g. |

If desired, the soybean meal can be replaced with alfalfa meal or corn gluten meal.

EXAMPLE 15

A cattle feed additive is prepared having the following composition:

| | |
|---|---|
| The formulation of Example 10 | 22.24 g. |
| feed excipient (Soybean meal, or corn gluten meal | 77.76 g. |
| | 100.00 g. |

EXAMPLE 16

A cattle bolus is prepared having the following composition:

| | |
|---|---|
| The formulation of Example 10 | 1.89 g. |
| Starch | 0.5–2.0 g. |
| Talc | 0.05–2.0 g. |
| Magnesium stearate | 0.05–2.0 g. |
| sodium chloride | 0.5–5.0 g. |
| lactose | 3.0–8.0 g. |

EXAMPLE 17

A cattle paste is prepared having the following composition:

| | |
|---|---|
| The formulation of Example 10 | 6% |
| Corn oil | 85–90% |
| Antioxidant (e.g., a mixture of butylated hydroxy anisole and butylated hydroxy toluene) | 0.1–0.5% |
| Benzoic acid | 0.3% |
| Thickener (e.g., Cabosil M-5) | 6–10% |

EXAMPLE 18

An equine paste is prepared having the following composition:

| | |
|---|---|
| The formulation of Example 10 | 48% |
| Vegetable oil (e.g., corn oil) | 40–60% |
| Other fatty acid glycerides | 10–20% |
| Antioxidant (e.g., a mixture of butylated hydroxy anisole and butylated hydroxy toluene) | 0.1–0.5% |
| Benzoic acid | 0.3% |
| Thickener, (e.g., Cabosil M-5) | 1–5% |
| | 100% |

EXAMPLE 19

An oral suspension for human use is prepared having the following composition:

| | |
|---|---|
| 1-methoxycarbonyl-3-n-butyl-7(8)-phenylsulfinyl-triazino-[1,2-a]benzimidazole | 2.5% |
| Benzoic acid | 0.3% |
| Veegum K | 3.0% |
| Citric acid | 0.4% |
| Sodium citrate | 0.8% |
| Sodium saccharin | 0.01% |
| Magnasweet 100 | 0.02% |
| Flavor | 0.03% |
| Color | 0.0025% |
| Water Q.S. | to 100% |

Benzoic acid, citric acid and saccharin citrate are dissolved in 90 ml of water which has been heated to 95°–100° C. Veegum K is added slowly and allowed to fully hydrate. The resultant suspension is cooled to room temperature and Magnasweet 100 and saccharin are added. The active drug is stirred in, color and flavor are added and the additional water added as necessary. The suspension is milled through a colloid mill to assure uniform dispension.

EXAMPLE 20

A tablet for human use is prepared having the following composition:

| | | |
|---|---|---|
| 1-methoxycarbonyl-3-n-butyl-7(8)-phenylsulfinyl-triazino-[1,2-a]benzimidazole | 40% | 100 mg |
| Starch | 15% | 37.5 mg |
| Magnesium stearate | 1% | 2.5 mg |
| Talc | 2% | 5.0 mg |
| Color (lake) | 0.24% | 0.6 mg |
| Lactose | 41.76% | 104.4 mg |
| | | 250.0 mg |
| Water | .08 ml | |

Half of the lactose is blended with the color lake, then the balance of lactose is added and blended. The active drug is added to the lactose blend aand mixed until uniform. The starch paste is prepared, granulated, screened and dried to the desired moisture content. The dried granulation is screened, lubricants are added and mixed. Tablets are then prepared on a suitable tablet press.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound selected from the group of compounds represented by the formula:

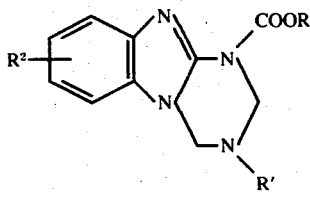

where R is a lower alkyl group having 1 to 4 carbon atoms; R' is diloweralkylaminoalkyl ($C_{2-6}$) or alkyl having 1 to 18 carbon atoms; $R^2$ is phenylsulfinyl, phenoxyethoxy, benzyloxyethoxy, methoxyethylsulfinyl, or 3-chloroprop-1-ylsulfinyl; the $R^2$-substitution being at the 7(8)-position; or a pharmaceutically acceptable salt thereof.

2. The compound of claim 1 wherein R is methyl.
3. The compound of claim 1 wherein R' is dimethylaminoethyl.
4. The compound of claim 1 wherein R' is n-butyl.
5. The compound of claim 1 wherein R' is n-nonyl.
6. The compound of claim 1 wherein $R^2$ is phenylsulfinyl.
7. The compound of claim 1 wherein $R^2$ is phenoxyethoxy.
8. The compound of claim 1 wherein $R^2$ is benzyloxyethoxy.
9. The compound of claim 1 wherein $R^2$ is methoxyethylsulfinyl.
10. The compound of claim 1 wherein $R^2$ is 3-chloroprop-1-ylsulfinyl.
11. The compound of claim 1 wherein said compound of Formula I is 1-methoxycarbonyl-3-n-butyl-7(8)-phenylsulfinyltriazino[1,2-a]benzimidazole.
12. The compound of claim 1 wherein said compound of Formula I is 1-methoxycarbonyl-3-n-nonyl-7(8)-phenylsulfinyltriazino[1,2-a]benzimidazole.
13. The compound of claim 1 wherein said compound of Formula I is 1-methoxycarbonyl-3-[2-(dimethylamino)ethyl]-7(8)-phenylsulfinyl-triazino[1,2-a]benzimidazole.
14. The compound of claim 1 wherein said compound of Formula I is 1-methoxycarbonyl-3-n-nonyl-7(8)-phenoxyethoxytriazino[1,2-a]benzimidazole.
15. A composition for controlling helminths in mammals comprising a pharmaceutically acceptable carrier and an anthelmintically effective amount of a compound selected from the group of compounds represented by the formula:

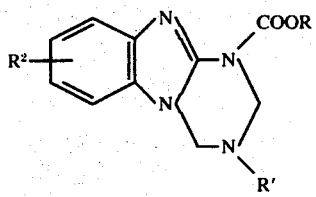

where R is lower alkyl group having 1 to 4 carbon atoms; R' is diloweralkylaminoalkyl ($C_{2-6}$) or alkyl having 1 to 18 carbon atoms; $R^2$ is phenylsulfinyl, phenoxyethoxy, benzyloxyethoxy, methoxyethylsulfinyl, or 3-chloroprop-1-ylsulfinyl; the $R^2$-substitution being at the 7(8)-position; or a pharmaceutically acceptable salt thereof.

16. The composition of claim 15 wherein R is methyl.
17. The composition of claim 15 wherein R' is dimethylaminoethyl.
18. The composition of claim 15 wherein R' is n-butyl.
19. The composition of claim 15 wherein R' is n-nonyl.
20. The composition of claim 15 wherein $R^2$ is phenylsulfinyl.
21. The composition of claim 15 wherein $R^2$ is phenoxyethoxy.
22. The composition of claim 15 wherein $R^2$ is benzyloxyethoxy.
23. The composition of claim 15 wherein $R^2$ is methoxyethylsulfinyl.
24. The composition of claim 15 wherein $R^2$ is 3-chloroprop-1-ylsulfinyl.
25. The composition of claim 15 wherein said compound of Formula I is 1-methoxycarbonyl-3-n-butyl-7(8)-phenylsulfinyltriazino[1,2-a]benzimidazole.
26. The composition of claim 15 wherein said compound of Formula I is 1-methoxycarbonyl-3-n-nonyl-7(8)-phenylsulfinyl-triazino[1,2-a]benzimidazole.
27. The composition of claim 15 wherein said compound of Formula I is 1-methoxycarbonyl-3-[2-(dimethylamino)ethyl]-7(8)-phenylsulfinyl-triazino[1,2-a]benzimidazole.
28. The composition of claim 15 wherein said compound of Formula I is 1-methoxycarbonyl-3-n-nonyl-7(8)-phenoxyethoxytriazino[1,2-]benzimidazole.
29. A method for controlling helminths in mammals which comprises administering an anthelmintically effective amount of a compound selected from the group of compounds represented by the formula:

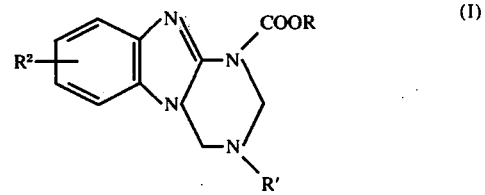

where R is a lower alkyl group having 1 to 4 carbon atoms; R' is a diloweralkylaminoalkyl ($C_{2-6}$) or alkyl having 1 to 18 carbon atoms; $R^2$ is phenylsulfinyl, phenoxyethoxy, benzyloxyethoxy, methoxyethylsulfinyl, or 3-chloroprop-1-ylsulfinyl; the $R^2$-substitution being at the 7(8)-position; or a pharmaceutically acceptable salt thereof.

30. The compound of claim 1 wherein R' is methyl.
31. The composition of claim 15 wherein R' is methyl.

* * * * *